US006995007B2

(12) United States Patent
Gunner et al.

(10) Patent No.: US 6,995,007 B2
(45) Date of Patent: Feb. 7, 2006

(54) ANTIFUNGAL BACTERIUM ATCC PTA-4838

(75) Inventors: Haim B. Gunner, Amherst, MA (US); Ming-Jung Coler, Amherst, MA (US); William A. Torello, S. Deerfield, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 10/608,582

(22) Filed: Jun. 23, 2003

(65) Prior Publication Data
US 2004/0043005 A1  Mar. 4, 2004

Related U.S. Application Data

(63) Continuation-in-part of application No. 10/324,240, filed on Dec. 19, 2002, now abandoned.

(60) Provisional application No. 60/343,513, filed on Dec. 21, 2001.

(51) Int. Cl.
*B09B 3/00*     (2006.01)
*A01N 63/00*    (2006.01)
*C12N 1/00*     (2006.01)
*C12N 1/12*     (2006.01)
*C12N 1/20*     (2006.01)

(52) U.S. Cl. ............... 435/252.1; 424/93.4; 435/262.5; 435/822

(58) Field of Classification Search ............... 424/93.1, 424/93.4; 435/262.5, 252.1, 822
See application file for complete search history.

(56) References Cited

U.S. PATENT DOCUMENTS

| 2,552,388 | A | * | 5/1951 | Allen et al. |
|---|---|---|---|---|
| 4,717,653 | A |   | 1/1988 | Webster, Jr. |
| 4,985,363 | A |   | 1/1991 | Inoue et al. |
| 5,068,105 | A |   | 11/1991 | Lewis et al. |
| 5,100,455 | A |   | 3/1992 | Pinckard et al. |
| 5,288,488 | A |   | 2/1994 | Backman et al. |
| 5,316,940 | A |   | 5/1994 | Georgiou et al. |
| 5,348,742 | A |   | 9/1994 | Howell et al. |
| 5,405,766 | A |   | 4/1995 | Kallury et al. |
| 5,496,547 | A |   | 3/1996 | Lam et al. |
| 5,543,301 | A |   | 8/1996 | Handelsman et al. |
| 5,570,973 | A |   | 11/1996 | Hunt |
| 5,626,437 | A |   | 5/1997 | Hunt et al. |
| 5,670,368 | A |   | 9/1997 | McLaughlin et al. |
| 5,698,028 | A | * | 12/1997 | Higa ............................. 71/11 |
| 5,714,507 | A |   | 2/1998 | Valcke et al. |
| 5,733,067 | A |   | 3/1998 | Hunt et al. |
| 5,756,087 | A |   | 5/1998 | Ligon et al. |
| 5,756,304 | A |   | 5/1998 | Jovanovich |
| 5,780,023 | A |   | 7/1998 | McLaughlin et al. |
| 5,863,789 | A | * | 1/1999 | Komatsu et al. ............ 435/262 |
| 5,900,236 | A |   | 5/1999 | Gerhardson et al. |
| 5,908,774 | A |   | 6/1999 | Shaw |
| 5,955,348 | A |   | 9/1999 | Ligon et al. |
| 5,972,689 | A |   | 10/1999 | Cook et al. |
| 5,980,747 | A |   | 11/1999 | Vandenbergh et al. |
| 6,060,051 | A |   | 5/2000 | Heins et al. |
| 6,077,505 | A |   | 6/2000 | Parke et al. |
| 6,103,875 | A |   | 8/2000 | Martinez-Miller et al. |
| 6,110,726 | A | * | 8/2000 | Roberts ................... 435/252.4 |
| 6,156,560 | A |   | 12/2000 | Chun |
| 6,204,049 | B1 |   | 3/2001 | Bennett et al. |
| 6,264,967 | B1 | * | 7/2001 | Ito et al. |
| 6,280,719 | B1 |   | 8/2001 | Suh |
| 6,312,940 | B1 |   | 11/2001 | Schisler et al. |
| 6,319,497 | B1 |   | 11/2001 | Casida, Jr. et al. |
| 6,455,035 | B1 |   | 9/2002 | Suri et al. |
| 6,503,746 | B1 | * | 1/2003 | Daane et al. ............. 435/252.1 |
| 6,649,408 | B2 | * | 11/2003 | Bailey et al. ................ 435/325 |

OTHER PUBLICATIONS

Alabouvette et al., "Recent Advances in the Biological Control of Fusarium Wilts," *Pestic. Sci.*, 1993, 37(4):365-373.

Ash et al., "Molecular identification of rRNA group 3 bacilli (Ash, Farrow, Wallbanks and Collins) using a PCR probe test, proposal for the creation of a new genus *Paenibacillus*," *Antonie van Leeuwenhoek*, 1993, 64:253-260.

AUW (Auburn University Website), PGPR and rhizobacteria. Biocontrol Institute, Auburn University, Auburn, AL, http://www.ag.auburn.edu/bci/pgpr.htm.

Bashan et al., "Proposal for the division of plant growth-promoting rhizobacteria into two classifications: biocontrol-PGPB (plant growth-promoting bacteria) and PGPB," *Soil Biol. Biochem.*, 1998, 30:1225-1228.

Batson, Jr. et al., "Vegetables," *Biological and Cultural Tests for Control of Plant Diseases*, 1999, 14:149-150, APS Press, St. Paul, MN.

Boland and Kuykendall (eds.), *Plant-Microbe Interactions and Biological Control*, 1998, Marcel Dekker, NY (TOC only).

Burgess and Keane, "Biological control of *Botrytis cinerea* on chickpea seed with *Trichoderma* spp. and *Gliocladium roseum*: indigenous versus non-indigenous isolates," *Plant Pathol.*, 1997, 46:910-918.

(Continued)

*Primary Examiner*—David M. Naff
*Assistant Examiner*—Deborah K. Ware
(74) *Attorney, Agent, or Firm*—Fish & Richardson P.C., P.A.

(57) ABSTRACT

A composition comprising bacteria and an inert carrier is disclosed. The carrier can be porous, ceramic particles. The composition can also include a growth medium. Bacteria in such a composition can comprise a novel strain designated APM-1. APM-1 is a Gram-positive, aerobic, motile rod, and appears to be most closely related to *Bacillus* spp. Also disclosed are methods of using the disclosed compositions for controlling plant fungal diseases, for controlling mammalian fungal diseases, or for bioremediation.

8 Claims, No Drawings

OTHER PUBLICATIONS

Cartwright and Benson, "Optimization of Biological Control of Rhizoctonia Stem Rot of Poinsettia by *Paecilomyces lilacinus* and *Pseudomonas cepacia*," *Plant Diseases*, 1995, 79:301-308.

Deacon, "Significance of Ecology in the Development of Biocontrol Agents against Soil-borne Plant Pathogens," *Biocontrol Science and Technology*, 1991, 1:5-20.

Handelsman and Stabb, "Biocontrol of Soilborne Plant Pathogens," *Plant Cell*, 1996, 8:1855-1869.

Haran et al., "Increased Constitutive Chitinase Activity in Transformed *Trichoderma harzianum*," *Biological Control*, 1993, 3:101-108.

Hardy et al., "Applications of the Acetylene-Ethylene Assay for Measurement of Nitrogen Fixation," *Soil Biol. Biochem.*, 1973, 5:47-81.

Herr, "Biological control of *Rhizoctonia solani* by binucleate *Rhizoctonia* spp. and hypovirulent *R. solani* agents," *Crop Protection*, 1995, 14:179-187.

Hino and Wilson, "Nitrogen Fixation by A-Facultative Bacillus," *J. Bacteriol.*, 1958, 75:403-408.

Hubner et al., "Types of *Listeria monocytogenes* predicted y the positions of EcoRi cleavage sites relative to ribosomal RNA sequences," *Proc. Natl. Acad. Sci. USA*, 1995, 92: 5234-5238.

James and Sutton, "Biological control of bortytis leaf blight of onion by *Gliocladium roseum* applied as sprays and with fabric applicators," *Eur. J. Plant Pathol.*, 1996, 102:265-275.

Jones and Samac, "Biological Control of Fungi Causing Alfalfa Seedling Damping-Off with a Disease-Suppressive Strain of *Streptomyces*," *Biological Control*, 1996, 7:196-204.

Kohl et al., "Biological Control of *Botrytis cinerea* in Cyclamen with *Ulocladium atrum* and *Gliocladium roseum* Under Commercial Growing Conditions," *Phytopathology*, 1998, 88:568-575.

Krieg, "Introduction to Systematics," *Methods for General and Molecular Bacteriology*, Gerhardt et al. (eds.), American Society for Microbiology, Washington, D.C., pp. 603-710.

Lemanceau and Alabouvette, "Biological control of fusarium diseases by fluorescent *Pseudomonas* and non-pathogenic *Fusarium*," *Crop Protection*, 1991, 10:279-286.

Limón et al., "Increased Antifungal Activity of *Trichoderma harzianum* Transformants That Overexpress a 33-kDa Chitinase," *Phytopathology*, 1999, 89:254-261.

Liu et al., "Biological Control of Potato Scab in the Field with Antagonistic *Streptomyces scabies*," *Phytopathology*, 1995, 85:827-831.

Lo et al., "Biological Control of Turfgrass Diseases with a Rhizosphere Competent Strain of *Trichoderma harzianum*," *Plant Disease*, 1996, 80:736-741.

Lodish et al., "Recombinant DNA Technology," *Molecular Cell Biology*, 3rd Edition, 1997, Scientific American Books, W.H. Freeman, NY, Chapter 7, pp. 221-261.

Lumdsen and Lewis, *Biotechnology of Fungi for Improving Plant Growth*, Whipps and Lumdsen (eds.), 1988, Cambridge University Press, UK, pp. 173-189.

McGrath, "Evaluation of *Gliocladium virens* as biocontrol agent for managing phytophthora in cucurbits," *Biological and Cultural Tests for Control of Plant Diseases*, 1994, vol. 10, p. 146, APS Press, St. Paul, MN.

Nielsen and Sorensen, "Multi-target and medium-independent fungal antagonism by hydrolytic enzymes in *Paenibacillus polymyxa* and *Bacillus pumilus* strains from barley rhizosphere," *FEMS Microbiology Ecology*, 1997, 22:183-192.

Pettersson et al., "Transfer of *Bacillus lentimorbus* and *Bacillus popillae* to the genus *Paenibacillus* with emended descriptions of *Paenibacillus lentimorbus* comb. nov. and *Paenibacillus popillae* comb. nov.," *International Journal of Systematic Bacteriology*, 1999, 49(2):531-538.

Piuru et al., "A novel antimicrobial activity of a *Paenibacillus polymyxa* strain isolated from regional fermented sausages," *Letters in Applied Microbiol.*, 1998, 27:9-13.

Postgate, "The Acetylene Reduction Test for Nitrogen Fixation," *Methods in Microbiology*, Norris and Ribbons (eds.), Academic Press, 1972, vol. 6B, pp. 343-356.

Quarles et al., *The IPM Practioner: Monitoring the Field of Pest Management*, 1999 Directory of Least-Toxic Pest Control Products, vol. XX, No. 11/12, Nov./Dec.

Rankin and Paulitz, "Evaluation of Rhizosphere Bacteria for Biological Control of Pythium Root Rot of Greenhouse Cucumbers in Hydroponic Culture," *Plant Disease*, 1994, 78(5):447-451.

Roebroeck and Mes, "Biological Control of *Fusarium* in Gladiolus with Non-Pathogenic *Fusarium* Isolates," *Acta Horticulturae*, 1992, 2(325):769-779.

Sambrook et al., *Molecular Cloning, A Laboratory Manual*, 2nd Edition, 1989, Cold Spring Harbor Laboratory Press, Plainview, NY (TOC only).

Stanghellini and Miller, "Biosurfactants: Their Identity and Potential Efficacy in the Biological Control of Zoosporic Plant Pathogens," *Plant Disease*, 1997, 81(1):4-12.

Stevenson and James, "Evaluation of biological control of early blight and late blight," *Biological and Cultural Tests for Control of Plant Diseases*, 1994, vol. 10, p. 89, APS Press, St. Paul, MN.

USDA, 1999, List of commercially-available biocontrol products, USDA website, www.barc.usda.gov/psi/bpdl/bioprod.htm—Washington, D.C.

Whipps, "Developments in the Biological Control of Soil-borne Plant Pathogens," *Advances in Botanical Research*, 1997, 26:1-134.

Yamaguchi et al., "Biocontrol of Fusarium Wilt of Tomato and Verticillium Wilt of Eggplant by Non-pathogenic *Fusarium oxysporum* MT0062," *Ann. Phytopath. Soc. Japan*, 1992, 58:188-194.

Yuen et al., "Biological Control of *Rhizoctonia solani* on Tall Fescue Using Fungal Antagonists," *Plant Disease*, 1994, 78(2):118-123.

* cited by examiner

US 6,995,007 B2

ANTIFUNGAL BACTERIUM ATCC PTA-4838

CROSS-REFERENCE TO RELATED APPLICATIONS

This application claims is a continuation-in-part of U.S. application Ser. No.: 10/324,240, filed on Dec. 19, 2002, now abandoned entitled "Novel Antifungal Bacterium And Compositions," which claims priority to U.S. application Ser. No.: 60/343,513, filed on Dec. 21, 2001, entitled "Novel Gram Positive Antifungal Bacterium," both of which are incorporated herein by reference.

TECHNICAL FIELD

This invention relates to compositions comprising an inert carrier material and a microorganism associated with the carrier material. More particularly, the invention relates to compositions comprising an inert carrier and a strain that exhibits fungicidal or fungistatic activity for control of plant diseases, a strain suitable for bioremediation, or a strain that exhibits fungicidal or fungistatic activity for control of pathogenic fungi of medical significance.

BACKGROUND

Soil-borne plant pathogenic fungi cause severe economic losses in the agricultural and horticultural industries. For example, root and crown rot diseases caused by soil-borne fungal pathogens such as *Pythium* spp. are a widespread and recurrent problem in plant production. As another example, *Rhizoctonia solani* is a major soil-borne fungal phytopathogen, and is associated with diseases such as damping-off, root rot, and leaf and stem rot in many plant species, including greenhouse crops. *R. solani* is also associated with brown patch in creeping bentgrass and various other turfgrasses of high commercial value. Species of *Alternaria* and *Fusarium* are associated with diseases such as early blight of tomato and *Fusarium* wilt of numerous fruit and vegetable crops.

In light of actual and potential environmental and health hazards associated with pesticide use, fungicide use may be restricted. As a result, growers have sought alternative approaches to disease control. These alternative approaches include the use of biological agents and disease-suppressive growing media. The use of biologically active agents in the control of plant pests and diseases has become especially important. Despite the recent commercialization of several types of microbial biocontrol agents, questions still remain about the ability of these agents to provide consistent and reliable control against fungal pathogens and insect pests.

The use of biologically active agents in the cleanup of toxic waste sites has become especially important. Despite attempts to identify microbial environmental control agents, questions still remain about the ability of these agents to provide consistent and reliable cleanup of toxic waste sites. Factors militating against the propagation and survival of microorganisms introduced into polluted soils include: competition with other organisms for nutrients, water and space; parasitism, antibiosis and predation by other organisms; and unfavorable physicochemical parameters of the soil milieu, including sub-optimal pH, water and oxygen concentrations. In the case of polluted soils, problems associated with survival and propagation of microorganisms introduced into such soil may be exacerbated by the presence of toxic pollutants at concentrations that are inimical to microbial growth. There has long been a need for microorganisms that have suitable bioremediation properties, e.g., bacteria that consume, over a period of time, accumulated hydrocarbons.

Current bioremediation methodology in the main employs the addition of nutrients to treatment sites to enhance the activity of in situ populations or by the treatment of above ground waste and solid sludges by methods including land farming, composting or slurry reactors. Absent, by and large, has been the practicability of applying organisms exogenously since these are rapidly eliminated by environmental constraints and existing populations. There is a strong interest in applying bioremediation approaches to remove toxic compounds from the environment.

Fungal infections can result in life-threatening infections in individuals, especially immunocompromised patients, such as persons suffering from AIDS or cancer. For example, *Mucor* infections present serious consequences to immunocompromised patients and to diabetics. *Mucor* infections often result in infection of the paranasal sinuses, with extension into the brain (rhinocerebral). Orbital infection may spread to involve the eye as well. Other complications include spread to the lung, skin and gastrointestinal tract. As another example, *Aspergillus* infections present primarily as pulmonary complications in immunocompromised patients, often resulting in a necrotizing pneumonia. There can be widespread dissemination to other organs.

Though various treatments are available, including, among others, nystatin, amphotericin B, haloprogin and sulfa derivatives, toxic affects are not uncommon; thus amphotericin B is toxic to the kidneys and treatment of mucocutaneous candidiasis with antibiotics alone has not met with success. Similar equivocal results are experienced with other treatments as well. The potential for a new treatment from a bacterium with demonstrated activity against a wide range of fungi may therefore be of significant therapeutic value.

SUMMARY

Novel compositions are disclosed for the biological control of fungal pathogens. In some embodiments, a composition can comprise an inert carrier and bacteria of a strain that exhibits fungicidal or fungistatic activity. A composition can also include a growth medium. In some embodiments, an inert carrier comprises porous ceramic particles and the bacteria comprise a strain that inhibits growth of a fungal plant pathogen. In some embodiments, the bacterial strain is a novel Gram-positive bacterium designated APM-1. The novel compositions and methods can be used, for example, to suppress diseases associated with soil-borne plant pathogenic fungi, e.g., *Rhizoctonia* species such as *R. solani*. The novel compositions and methods can also be effective in suppressing plant diseases associated with *Pythium, Alternaria* and *Fusarium* species.

Thus, in one aspect, the invention comprises a biologically pure culture of a microorganism having the identifying characteristics of a Gram-positive bacterium designated APM-1, deposited as ATCC Accession No. PTA-4838 on Dec. 2, 2002, with The American Type Culture Collection, P.O. Box 1549,Manassas, Va. 20108.

In another aspect, the invention features a composition comprising a bacterial strain that exhibits fungicidal or fungistatic activity combined with an inert carrier. The bacterial strain is present at about $10^2$ cfu to about $10^{11}$ cfu per gram of carrier. Such a composition can be in granular form. In some embodiments, the bacterial strain exhibits fungicidal or fungistatic activity towards a fungal plant pathogen, e.g., the bacterial strain can be APM-1. The fungus against which fungicidal or fungistatic activity is observed can be, for example, a *Rhizoctonia* species; a *Pythium* species; a *Fusarium* species; an *Alternaria* species; or a *Sclerotinia* species.

In some embodiments, the inert carrier can be porous, ceramic particles, e.g., diatomaceous earth particles stabilized and calcined at high temperatures. The inert carrier can have a pore size distribution such that from about 20% to about 100% of the particles have a pore size of from about 0.5 microns (µm) to about 5 microns.

In some embodiments, a composition of the invention also includes a growth medium, e.g., about 5% to about 40% growth medium/carrier on a weight/weight, dry basis.

The invention also features a method of controlling or suppressing the growth of a plant pathogenic fungus. In some embodiments, the method comprises applying an effective amount of a bacterial strain designated APM-1, to an environment in which the plant pathogenic fungus may grow. In other embodiments, the method comprises applying an effective amount of a composition to an environment in which the plant pathogenic fungus may grow. Such a composition comprises a bacterial strain that exhibits fungicidal or fungistatic activity combined with an inert carrier. The composition can include a growth medium. The fungus can be a *Rhizoctonia* species, a *Pythium* species, a *Fusarium* species, an *Alternaria* species, or a *Sclerotinia* species.

The invention also features a method of controlling the growth of a plant pathogenic fungus. The method involves applying a composition to a plant. The composition comprises a bacterial strain that exhibits fungicidal or fungistatic activity combined with an inert carrier and, optionally, a growth medium. The bacterial strain can be APM-1. In the method, symptoms of a disease caused by the fungus are ameliorated or suppressed on the plant. The composition can be applied to the leaves or stem of the plant, e.g., the leaves of a creeping bentgrass species or the stem of a vegetable crop.

The invention also features a method of controlling the growth of a plant pathogenic fungus, which comprises applying a composition to soil. The composition comprises a bacterial strain that exhibits fungicidal or fungistatic activity combined with an inert carrier and, optionally, a growth medium. The bacterial strain can be APM-1. In the method, symptoms of a disease associated with the fungus are ameliorated or suppressed on a plant growing in the soil. The fungus can be a *Rhizoctonia* species, a *Pythium* species, a *Fusarium* species, an *Alternaria* species, or a *Sclerotinia* species.

In another aspect, the invention features a composition comprising about $10^3$ cfu to about $10^{11}$ cfu per gram dry inert carrier of a bacterial strain that exhibits degradative activity towards a toxin. The carrier can comprise porous, ceramic particles. For example, from about 20% to about 100% of the particles can have a pore size of from about 0.5 µm to about 5 µm. The composition can further comprise about 5% to about 40% growth medium per gram of carrier on a wt/wt dry basis.

The invention also features a method of reducing the amount of a toxin in an environment, comprising applying an effective amount of a composition to that environment. The composition can comprise about $10^3$ cfu to about $10^{11}$ cfu per gram dry inert carrier of a bacterial strain that exhibits degradative activity towards a toxin. The toxin can be trichloroethylene, methylene chloride, or toxaphene. The environment can be soil, a marine environment, or a toxic waste dump.

The invention also features a method of degrading a toxin. The method comprises applying a composition comprising about $10^3$ cfu to about $10^{11}$ cfu per gram dry inert carrier of a bacterial strain that exhibits degradative activity towards a toxin, to an environment where the toxin may be present. The amount of a toxin present in the environment is decreased or eliminated. The composition can be applied to soil.

In another aspect, the invention features a method of identifying an inhibitor of a mammalian pathogenic fungus. The method comprises contacting a Gram-positive bacterium designated APM-1 with the fungus, and measuring whether growth of the pathogenic fungus is inhibited. Alternatively, the method comprises contacting an extract from APM-1 with the fungus, and measuring whether growth of the pathogenic fungus is inhibited. The extract can be an aqueous extract or a methanolic extract. The fungus can be a *Microsporum, Trichophyton* or *Epidermophyton* species, a *Cladosporium* or *Trichosporon* species, or a *Candida* or *Aspergillus* species. The fungal pathogen can be a human fungal pathogen, or a fungal pathogen of dogs, cats, cattle, pigs, or sheep.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

APM-1

APM-1 is an aerobic, spore-forming, Gram-positive motile rod. The characteristics of the fatty acids in purified APM-1 indicate that APM-1 is related to *Bacillus lentimorbus*. However, APM-1 also appears to be related to *Paenibacillus macerans*. It is of interest that nitrogen-fixing bacteria in the genus *Bacillus* recently were reassigned to the genus *Paenibacillus*. Other identifying characteristics of APM-1 indicate that APM-1 is related to *Bacillus amyloliquefaciens*. Collectively, the data suggest that APM-1, although similar to species in the *Bacillus* or *Paenibacillus* genera, is a new, unique bacterial strain.

APM-1 is an effective biological control organism that has fungicidal activity, and may also have fungistatic activity. APM-1 provides good fungal disease suppression and maintains high overall plant quality. The use of APM-1 as a biocontrol agent can reduce or eliminate the use of environmentally harmful pesticides or fungicides.

In one aspect of the invention, APM-1 can be used as a solid. For example, a culture of APM-1 is grown in a suitable growth medium, the bacteria separated from the spent medium, resuspended in a fresh medium and the bacteria spray-dried. The resulting powder can be used, e.g., as a dusting biocontrol agent on vegetable crops. Alternatively, APM-1 can be used as a liquid, e.g., a culture of APM-1 can be grown in a suitable growth medium, the bacteria separated from the spent medium, and resuspended in water, buffer or fresh medium. The resulting suspension can be used, e.g., as a foliar spray on turfgrass.

In another aspect of the invention, APM-1 can be combined with one or more compounds to form a mixture suitable for applying to an environment in which a plant pathogenic fungus can grow. Compounds that can be combined with APM-1 bacteria include fertilizers, micronutrient donors, surfactants, or adjuvants conventionally employed in the art of formulation. See, e.g., U.S. Pat. Nos. 6,280,719; 5,780,023; 5,765,087; 5,348,742; and 5,068,105. The number of compounds selected for a given mixture are chosen in accordance with the intended objectives and the prevailing circumstances. For example, if a mixture is intended to be applied to a golf green, the mixture can include a fertilizer, APM-1, and surfactants.

The resulting mixture can be a solid or a liquid, e.g., an emulsifiable concentrate, a coatable paste, a directly sprayable solution, a dilutable solution, a dilute emulsion, a wettable powder, a dusting powder, a granular formulation, or an encapsulated formulation.

Compositions

In another aspect of the invention, bacteria can be combined with an inert carrier to form a composition suitable for applying to soil. In such a composition, bacteria constitute from about $10^2$ colony-forming units to about $10^{11}$ colony-forming units per gram of air-dry carrier, e.g., from about $10^3$ to about $10^{10}$ cfu, from about $10^4$ to about $10^{10}$ cfu, from about $10^5$ to about $10^{10}$ cfu, from about $10^6$ to about $10^{10}$ cfu, from about $10^7$ to about $10^{10}$ cfu, or from about $10^7$ to about $10^9$ cfu per gram of air-dry carrier. Inert carrier can constitute the major remaining component in the composition. In some embodiments, the composition consists essentially of bacteria and inert carrier.

An inert carrier typically is used in granular form. In some embodiments, an inert carrier can be vermiculite or silica gel. See, e.g., U.S. Pat. Nos. 6,280,719, 5,780,023, 5,348,742, and 5,068,105. In some embodiments, an inert carrier comprises porous, ceramic particles. The main component of certain porous, ceramic particles is diatomaceous earth. These particles contain a stable and continuous network of pores to support a sustained population of bacteria. Suitable porous, ceramic particles include particles sold under the following trade names: AXIS™ (Eagle-Pritchard, Reno, Nev.), PROFILE™ (Aimcor, Buffalo Grove, Ill.) and ISO-LITE® (Sumitomo, Nanao-Shi, Japan). The main component of AXIS™ particles is diatomaceous earth. The main components of PROFILE™ particles are $SiO_2$ and illite clay. The main components of ISOLITE® particles are SiO, AlO and FeO.

Porous, ceramic particles can be extruded to a diameter from about 1 mm to about 10 mm, and then kiln-fired. Each particle can have a roughly cylindrical shape. The specific surface area can be about 4.6 $m^2$/gram, using American Society of Testing and Materials method C1274-00 and the multipoint equation of Branauer, Emmitt and Teller (BET). The density can be about 32 lbs/ft$^3$ (0.51 g/cm$^3$). The porosity can be about 74%, with a minimum porosity of about 70%. A typical pore size distribution is as follows: 6% are <0.5 micrometers ($\mu$), 12% are 0.5–1.0$\mu$, 43% are 1–3$\mu$ and 39% are >3$\mu$. In general, from about 20% to about 100% of the pores are from 0.5$\mu$ to 5$\mu$. For example, the pore size distribution can be such that from about 25% to 85% of the pores are from 0.5$\mu$ to 5$\mu$, or about 30% to 75% of the pores are from 0.5 to 5$\mu$, or about 45% to 75% of the pores are from 0.5 to 5$\mu$. The maximum size typically is about 15 to about 20$\mu$. The pores typically are continuous, open-ended and interconnecting, which minimizes the amount of dead-end pore space. Such particles typically are chemically inert and have a degradation loss of less than 2% when measured by American Society of Testing and Materials method ASTM-88. In the case of ISOLITE® OR ISOLITE®-like particles, the chemical composition can be, by weight, about 78% $SiO_2$, about 12% $Al_2O_3$ and about 5% by $Fe_2O_3$. Other components typically are present at less than 5% by weight, e.g., CaO at about 2%, and MgO, $K_2O$, NaO and $TiO_2$ at less than about 2%.

All of the bacteria in a composition can belong to a single bacterial strain. Alternatively, bacteria of a single strain can constitute a percentage of the bacteria in a composition. For example, about 5% or less, 10% or less, 20% or less, 30% or less, 40% or less, 50% or less, 60% or less, 70% or less, 80% or less, or 90% or less of the bacteria in a composition can be bacteria of a given strain. The percentage of bacteria of a given strain in a composition is measured as the number of colony-forming units of that strain divided by the total colony-forming units for all bacteria. A desired proportion of different strains of bacteria to be used in a composition can be readily determined by measuring the level of biocontrol achieved at various proportions and using the proportion that provides optimum control of a given pathogen.

Bacteria for use in a composition of the invention exhibit fungicidal or fungistatic activity against one or more fungal pathogens of plants or animals. For example, bacteria exhibiting fungicidal or fungistatic activity against a fungal plant pathogen can be used to inhibit growth of that pathogen and thus provide effective biological control. Methods are known for identifying the spectrum of fungicidal and/or fungistatic activity of bacteria. Bacteria that can be used in a composition include Gram-positive bacterial strains, e.g., APM-1 or *Bacillus* species, and Gram-negative bacterial strains such as *Pseudomonas* species. See, e.g., U.S. Pat. Nos. 5,543,301; 5,496,547; 5,756,087; 5,670,368; 5,972,689; 6,455,035; 5,900,236; 5,955,348; 6,103,875; 6,156,560; 6,060,051; and 6,319,497.

It is contemplated that a proportion of the bacteria in a composition can be relatively innocuous bacterial strains that do not exhibit significant fungicidal or fungistatic activity. Relatively innocuous bacterial strains may be advantageous in some embodiments, e.g., as a marker for persistence in the environment or as a marker for effective coverage following spray application of a composition.

In some embodiments, a growth medium is also included in the composition, e.g., a composition of the invention includes bacteria, porous ceramic particles and a growth medium. The amount of growth medium present in a composition can be from about 5% to about 40% per gram inert carrier on a dry, weight to weight basis, e.g., from about 5% to about 35%, or about 10% to about 30%, or about 10% to about 25% growth medium/inert carrier on a dry weight to weight basis. Without being bound by theory, it is believed that a composition that includes a growth medium provides the bacterium with a nutrient-rich micro-environment, resulting in a competitive advantage to bacteria present in the composition compared to native soil bacteria thus enabling bacteria of the composition to function more effectively as biocontrol agents. Suitable growth media include, without limitation, Trypticase Soy Broth (TSB), Soy Flour Broth, Luria Broth isolated soy protein, dairy hydrolysates, meat hydrolysates, grain flour broths, vegetable hydrolysates, or yeast extracts.

In some embodiments, an amount of water is present in the composition. The amount of water present in a composition can be from about 1% to about 15% per gram inert carrier, e.g., from about 5% to about 13%, or from about 7% to about 13% on a weight to weight basis.

Methods of Suppressing Fungal Disease

The invention also features a method comprising applying a composition of the invention to an environment in which a plant pathogenic fungus may grow. Such an environment can be soil, a plant seed, a plant, or a plant part (e.g., leaves, roots, branches and stems). The composition typically is applied in an amount effective to control or suppress fungal growth, e.g., in an amount sufficient to control or suppress observable symptoms on a plant of a fungal disease. The rate of application may vary according to the plant species to be protected, the efficacy of the bacterial strain against the pathogen to be controlled, and the severity of the disease pressure. Typically, the rate of application is about $1.3 \times 10^5$ cfu/cm$^2$ to about $1.3 \times 10^{10}$ cfu/cm$^2$, or about $1.3 \times 10^6$ cfu/cm$^2$ to about $1.3 \times 10^9$ cfu/cm$^2$, or about $1.3 \times 10^7$ cfu/cm$^2$ to about $1.3 \times 10^8$ cfu/cm$^2$. Like the nature of the composition, a method of application such as spraying, atomizing, dusting, scattering or pouring, is chosen in accordance with the intended objectives and the prevailing circumstances.

Particularly suitable methods for applying a composition include methods that involve seed coating, soil application or incorporation into a growth medium. The number of times that a composition is applied may vary, depending on the observed or expected intensity of infestation by a particular fungal pathogen. A composition can be applied to soil as a liquid, but can also be applied to soil in granular form. Outdoor soil applications can be in furrow, broadcast, or soil injection. In greenhouse or other indoor environments, a composition can be applied by mixing with potting soils typically used in such environments. A composition may also be applied to seeds by impregnating the seeds with a liquid formulation, or coating them with a solid formulation. In special cases, further types of application are also possible, for example, selective treatment of individual plant stems or buds.

A suitable group of plants with which to practice the invention include dicots, such as safflower, alfalfa, soybean, or sunflower. Also suitable are monocots such as Kentucky bluegrass (*Poa pratensis*), creeping bentgrass (*Agrostris palustris*), corn, wheat, rye, barley, or oat. Also suitable are vegetable crops or root crops such as potato, broccoli, peas, peppers, lettuce, sweet corn, popcorn, tomato, beans (including kidney beans, lima beans, dry beans, green beans) and the like. Thus, the invention has use over a broad range of plants, including species from the genera *Agroslis, Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypiuni, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panicum, Pannesetum, Persea, Phaseolus, Pistachia, Pisum, Poa, Pyrus, Prunus, Raphanus, Ricinus, Secale, Senecio, Sinapis, Solanum, Sorghum, Theobromus, Trigonella, Triticum, Vicia, Vitis, Vigna* and *Zea*.

Plant pathogenic fungi whose disease symptoms can be controlled or suppressed include *Pythium aphanidermatum, Sclerotinia homeocarpa* and *Rhizoctonia solani, Fusarium oxysporum, Alternaria* spp. Diseases associated with these fungi include damping-off, dollar spot, and brown patch.

Bioremediation Compositions and Methods

The invention also features compositions suitable for use in bioremediation. Microorganisms for use in a composition of the invention exhibit toxin-degrading activity against one or more toxic compounds. Compositions suitable for bioremediation comprise an inert carrier, a strain of microorganism that exhibits toxin-degrading activity and, optionally, a growth medium. The inert carrier is an inert carrier as described above, e.g., porous, ceramic particles having a typical pore size distribution as follows: 6% are<0.5 micrometers ($\mu$), 12% are 0.5–1.0$\mu$, 43% are 1–3$\mu$ and 39% are>3$\mu$. In general, from about 20% to about 100% of the pores are from 0.5$\mu$ to 5$\mu$. A growth medium can be as described above, e.g., Trypticase Soy Broth (TSB), Soy Flour Broth, Luria Broth isolated soy protein, dairy hydrolysates, meat hydrolysates, grain flour broths, vegetable hydrolysates, or yeast extracts. The proportions of each component in a composition can be as described above. For example, bacteria can constitute from about $10^2$ colony-forming units to about $10^{11}$ colony-forming units per gram of air-dry carrier, e.g., from about $10^3$ to about $10^{10}$ cfu, from about $10^4$ to about $10^{10}$ cfu, from about $10^5$ to about $10^{10}$ cfu, from about $10^6$ to about $10^{10}$ cfu, from about $10^7$ to about $10^{10}$ cfu, or from about $10^7$ to about $10^9$ cfu per gram of air-dry carrier. Inert carrier can constitute the major remaining component in the composition.

A bioremediation composition can contain microorganisms of a single strain or can contain microorganisms of more than one strain, provided that at least one strain exhibits toxin-degrading activity. Methods are known for identifying the spectrum of toxin-degrading activity of microorganisms. See, e.g., U.S. Pat. No. 5,756,304. For example, many microorganisms degrade polyaromatic hydrocarbons. Bacteria that degrade 2–3 ring low molecular weight polyaromatic hydrocarbons, such as naphthalene, phenanthrene, bi-phenyl and fluorene, include Gram negative genera such as *Pseudomonas, Burkholderia, Alcaligenes, Sphingomonas, Vibrio* and *Comamonas*. Gram-positive species such as *Mycobacterium, Nocardia, Rhodococcus* and *Gordona* are also known to degrade low molecular weight polyaromatic hydrocarbons. Bacteria that can be used in a composition include Gram-positive bacterial strains, e.g., *Bacillus* species, and Gram-negative bacterial strains such as *Pseudomonas putida* var. STM-603 (FERM BP-1751), *Pseudomonas* sp. STM-801 (FERM BP-1749), *Pseudomonas* sp. STM-904 (FERM BP-1750), *Pseudomonas putida* NRRL-B-18118, and *Pseudomonas putida* NRRL-B-15078. Other microorganisms that can be used include methanotrophic bacteria such as *Methylosinus trichosporium*. Other microorganisms that can be used include fungi such as white rot fungi. See, e.g., U.S. Pat. Nos. 6,503,746, 5,316,940; 4,985,363, 6,204,049, 5,908, 774, 5,100,455 and 5,980,747.

Toxic compounds that can be degraded include polyaromatic hydrocarbons, benzo[a]pyrene, chlorinated aliphatic solvents such as trichlorethylene and chloroform, mineral oils, petroleum fuel hydrocarbons such as crude oil and light oil, aliphatic hydrocarbons, alicyclic hydrocarbons, polychlorinated biphenyls, aromatic hydrocarbons, alcohols, ethers and ketones, herbicides, insecticides, DDT, dieldrin, toxaphene, 1,1,1-trichloroethane, 1,1 dichloroethane, trans-1,2 dichloroethene, trichloroethylene, and methylene chloride. Examples of organochlorine pesticide toxins are toxaphene, dieldrin, lindane, aldrin, chlordane, endrin, endrin aldehyde, heptachlor, heptachlor epoxide, and alpha-BHC, beta-BHC, gamma-BHC, delta-BHC, 4,4'-DDD, 4,4'-DDE, 4,4'-DDT, endosulfan I, endosulfan II, and endosulfan sulfate.

Sites suitable for bioremediation treatment with a composition may be solid or liquid. Sites may be treated in situ or removed from their location and treated elsewhere. Contaminated sites that may be treated with compositions of the invention include, but are not limited to, harbor dredge spoils, sediments, wastewater, sea water, soil, paper mills, sludge and refinery wastes, oil storage tanks and chemical storage tanks It is contemplated that a proportion of the microorganisms in a composition can be relatively innocuous strains that do not exhibit significant toxin-degrading activity. Relatively innocuous strains may be advantageous in some embodiments, e.g., as a marker for persistence in the environment or as a marker for effective coverage following spray application of a composition. A desired proportion of different strains of microorganisms to be used in a composition can be readily determined by measuring the rate and/or amount of toxin degradation achieved at various proportions and using the proportion that provides optimum bioremediation of a given environment.

As mentioned above, a growth medium can be included in the composition, e.g., a composition of the invention includes bacteria, porous ceramic particles and a growth medium. The amount of growth medium present in a composition can be from about 5% to about 40% per gram inert carrier on a dry, weight to weight basis, e.g., from about 5% to about 35%, or about 10% to about 30%, or about 10% to about 25% growth medium/inert carrier on a dry weight to weight basis. Without being bound by theory, it is believed that a composition that includes a growth medium provides the microorganisms with a nutrient-rich micro-environment, resulting in a competitive advantage to microorganisms present in the composition compared to native microorganisms thus enabling microorganisms of the composition to function more effectively as bioremediation agents. Suitable growth media include, without limitation, Trypticase Soy Broth (TSB), Soy Flour Broth, Luria Broth isolated soy protein, dairy hydrolysates, meat hydrolysates, grain flour broths, vegetable hydrolysates, or yeast extracts.

In some embodiments, an amount of water is present in the composition. The amount of water present in a composition can be from about 1% to about 15% per gram inert carrier, e.g., from about 5% to about 13%, or from about 7% to about 13% on a weight to weight basis.

The invention also features a method comprising applying a composition of the invention to an environment in which a toxin may be present. Such an environment can be soil, a landfill, a toxic waste dump, or contaminated groundwater. The composition typically is applied in an amount effective to degrade the toxin, e.g., in an amount sufficient to reduce or even eliminate the amount of detectable toxin present in a sample from the site where the composition was applied. The rate of application may vary according to the toxin(s) to be degraded, the efficacy of the microorganism strain against the toxin(s), the capacity of the microorganism(s) to withstand the toxic effects of the pollutant compounds, and the amount of the toxin initially present at the site. Typically, the rate of application is about $1.3\times10^5$ cfu/$cm^2$ to about $1.3\times10^{10}$ cfu/$cm^2$, or about $1.3\times10^6$ cfu/$cm^2$ to about $1.3\times10^9$ cfu/$cm^2$, or about $1.3\times10^7$ cfu/$cm^2$ to about $1.3\times10^8$ cfu/$cm^2$. Like the nature of the composition, a method of application such as spraying, atomizing, dusting, scattering or pouring, is chosen in accordance with the intended objectives and the prevailing circumstances. A composition can be applied to soil as a liquid, but can also be applied to soil in granular form. Soil applications can be in furrow, broadcast, or soil injection. In special cases, further types of application are also possible, for example, selective treatment of landfills or toxic waste dumps.

Methods of Controlling Fungal Disease

The invention also features methods for control of mammalian pathogenic fungi. Thus, the invention also features a method of identifying an inhibitor of a mammalian pathogenic fungus, comprising: contacting a Gram-positive bacterium designated APM-1, or an extract from APM-1, with the fungus; and measuring whether growth of the pathogenic fungus is inhibited. The bacteria or extract typically is applied in an amount effective to determine whether fungal growth is control or suppressed, e.g., in an amount sufficient to observe whether symptoms of fungal inhibition or death have occurred. An extract of APM-1 can be an aqueous extract, a methanolic or ethanolic extract, or an organic solvent extract, e.g, a benzene, hexane extract, or acetic acid ethyl ester and acetone extract. Extracts can also be obtained by treatment of bacterial lysates with n-pentane and steam distillation. Bacteria or extract can be contacted with fungi, for example, on a semi-solid medium or in a liquid medium. In some embodiments, bacteria or extract are contacted with mammalian tissue or cells that are infected with fungi, e.g., fungi-infected skin tissue from a human or fibroblast cells infected with a fungus. Bacteria or extract can be contacted with fungi once or more than once, depending on the observed or expected intensity of infestation by a particular fungal pathogen.

Fungi that may be tested or screened by such methods include fungi that cause systemic mycoses: histoplasmosis, coccidioidomycosis, blastomycosis, paracoccidioidomycosis and cryptococcosis, subcutaneous mycoses including sporotrichosis, chromoblastomycosis and maduromycosis. Mammalian pathogenic fungi that can be tested include *Pythium aphanidermatum, Sclerotinia homeocarpa* and *Rhizoctonia solani, Fusarium oxysporum, Alternaria* spp. Diseases associated with these fungi include systemic mycoses such as histoplasmosis, coccidioidomycosis, blastomycosis, paracoccidioidomycosis and cryptococcosis. Other diseases include subcutaneous mycoses such as sporotrichosis, chromoblastomycosis and maduromycosis. Cutaneous mycoses associated with these fungi include *Microsporum, Trichophyton* and *Epidermophyton* spp. Superficial mycoses associated with these fungi include *Cladosporium* and *Trichosporon* spp. Opportunistic fungal pathogens that may be tested include *Candida* and *Aspergillus* and the bacteria *Actinomyces* and *Nocardia.* Other pathogenic fungi include strains of *Aspergillus oryzae, Aspergillus terreus, Aspergillus versicolor, Cladosporium hergbarum, Stachybotrys chartarum, Penicillium aurantiogriseum, Penicillium chrsogenum, Penicillium glabrum* and *Fusarium oxysporum.* The bacteria or extract may act by suppression through competitive exclusion, by antagonistic action via metabolite release, by antibiotic action, or by a combination of mechanisms.

The invention will be further described in the following examples, which do not limit the scope of the invention described in the claims.

EXAMPLE 1

Isolation of APM-1

APM-1 was identified as a contaminant in grain flour media used to culture entomophagous fungi. APM-1 was biologically purified by repeated quadrant streaking on trypticase soy agar plates to obtain a single colony isolate. APM-1 was observed to be an aerobic, spore-forming, gram-positive motile rod. Fatty acid analysis of a sample of the purified organism was carried out by two commercial laboratories. One analysis suggested that APM-1 is most closely related to *Bacillus lentimorbus,* with a similarity index of 0.768. A similarity index of 0.6 is considered to be a close match. Fatty acid analysis by the other commercial laboratory suggested that APM-1 is most closely related to *Paenibacillus macerans,* with a similarity index of 0.572. However, APM-1 is not identical to either species. Collectively, the fatty acid characteristics show that APM-1 is a novel bacterial strain.

Two samples of APM-1 were submitted to a commercial laboratory for ribotyping analysis of 16S RNA. See, e.g., U.S. Pat. No. 4,717,653. The results indicated that the two samples had a mean similarity of 0.99 to each other. As shown in Table 1, the results also indicated that APM-1 was more similar to *Bacillus subtilis* than to *B. amyloliquefaciens* or ATCC 23350.

TABLE 1

Ribotyping Characteristics of APM-1

| Bacteria | Mean Similarity to APM-1 |
|---|---|
| *Bacillus subtilis* strain 1 | 0.84 |
| *Bacillus subtilis strain 2* | 0.82 |
| *Bacillus amyloliquefaciens* | 0.77 |
| ATCC 23350 (*B. amyloliquefaciens*) | 0.76 |

A sample of APM-1 was also submitted to a commercial laboratory for 16S rRNA gene sequence analysis. The 16S rRNA gene was PCR amplified from genomic DNA isolated from APM-1. One set of PCR primers corresponded to *E. coli* positions 005 and 1540. A second set of PCR primers corresponded to *E. coli* positions 005 and 0531. The nucleotide sequences of the APM-1 PCR products were aligned to sequences of 16S rRNA genes from known bacterial strains, using MicroSeq™ microbial analysis software and database. The results, shown in Table 2, indicate that the characteristics of APM-1 16S rRNA gene sequences are more similar to those of *B. amyloliquefaciens* than to those of the other strains in the database.

TABLE 2

16S rRNA Genetic Distance Characteristics of APM-1

| Bacteria | Genetic Distance from APM-1 16S rRNA Genes |
|---|---|
| *Bacillus amyloliquefaciens* | .37% |
| *Bacillus atrophaeus* | .56% |
| *Bacillus popilliae* | .93% |
| *Bacillus subtilis subtilis* | 1.03% |
| *Bacillus mojavensis* | 1.21% |
| *Brevibacterium halotolerans* | 1.40% |
| *Bacillus licheniformis* | 2.90% |
| *Bacillus pseudofirmus* | 5.14% |
| *Bacillus pumilus* | 5.15% |
| *Bacillus oleronius* | 5.23% |

APM-1 was tested with a commercially-available multi-well system from Biolog™ (Biolog, Inc., Hayward, Calif.) according to the manufacturer's instructions. The test characterizes substrate utilization characteristics, and physiological and metabolic characteristics of APM-1. The results indicated that APM-1 was most similar to *B. amyloliquefaciens.*

EXAMPLE 2

Preparation of APM-1 Inoculated Particles

APM-1 was inoculated into Trypticase Soy Broth (TSB) and incubated with shaking for 24 hours. At this time, the culture had reached a density of approximately $10^7$ to $10^9$ colony-forming units (cfu) per ml of culture.

Soy flour broth was prepared at a ratio of 5 gm soy flour (Archer-Daniels-Midland, Decatur, Ill.) to 100 ml water. The broth was sterilized by autoclaving for 20 minutes at 250° C. at 15 psi. APM-1 inoculant was made by adding 2 ml of the APM-1 overnight culture per 10 ml of soy flour broth.

A composition comprising APM-1, soy flour broth, and porous ceramic particles was formed by mixing 5 gm of porous ceramic particles (PROFILE™, Aimcor, Buffalo Grove, Ill.) per 10 ml of APM-1 inoculant. A second composition was formed by mixing 3 gm of AXIS™-XT (Eagle-Pritchard, Reno, Nev.) per 10 ml of APM-1 inoculant. Both compositions were air-dried in a laminar flow hood at room temperature for 48 to 72 hours. The pore size distribution of various porous ceramic particles is shown in Table 3. The median pore size for these same particles is shown in Table 4.

TABLE 3

Pore size distribution chart of various ceramic particles.

| Pore Size Diameter | ISOLITE ® CG-1 | PROFILE ™ | ISOLITE ® CG-2 | AXIS ™-XT |
|---|---|---|---|---|
| <.5μ to 1.0μ | 9%[a] | 78% | 6% | 58% |
| .5μ to 1.0μ | 19% | 4% | 12% | 9% |
| 1.0μ to 2.0μ | 33% | 2% | 27% | 5% |
| 2.0μ to 3.0μ | 12% | 2% | 16% | 5% |
| 3.0μ to 4.0μ | 5% | 2% | 7% | 5% |
| 4.0μ to 5.0μ | 4% | 2% | 4% | 5% |
| >5.0μ | 18%[b] | 10%[c] | 28%[d] | 13%[e] |

[a] % of pores having indicated diameter intervals.
[b] maximum diameter of 20.47μ.
[c] maximum diameter of 30μ.
[d] maximum diameter of 16.67μ.
[e] maximum diameter of 16.10μ.

TABLE 4

Median Pore Space

| | ISOLITE ® CG-1 | PROFILE ™ | ISOLITE ® CG-2 | AXIS ™-XT |
|---|---|---|---|---|
| Median Pore Space[a] | 1.189 | 0.078 | 1.367 | 0.314 |

[a] Volume in microns

EXAMPLE 3

Effect of APM-1 on Fungal Growth In Vitro

APM-1 was grown overnight on three types of media: nutrient broth, potato dextrose broth and trypticase soy broth. Six sterilized filter discs were placed around the petri plate about 0.8 cm from the edge. Ten μl of a stationary phase bacterial suspension were inoculated onto disc. (A Rhizoctonia colonized rice grain was placed in the center of each plate.) Sterilized media without APM-1 were used as controls. Plates were incubated for seven days. APM-1 was observed to inhibit fungal pathogen by exhibiting clearance zone of 0.3 to 0.5 cm around the disc containing the culture whereas the controls exhibited no clearance zone.

APM-1 inoculated particles were prepared as described in Example 2, using PROFILE™ particles. The potato dextrose agar plate was divided into two sections. APM-1 inoculated particles were broadcast on one half of the plate and the other half received un-inoculated particles. A *Rhizoctonia solani* colonized rice grain was placed in the center of the plate. The plate was incubated for seven days. The APM-1 treated particles were observed to suppress the growth of *Rhizocionia solani* under these conditions, whereas the untreated particles showed no inhibition of the fungus. Inhibition by APM-1 inoculated particles was also evident under the same conditions when the plate contained non-nutritive agar medium. The results observed on non-nutritive agar medium may be similar to the effect that would be observed under nutrient-deficient soil conditions.

EXAMPLE 4

Effect of APM-1 on Fungal Growth in Greenhouse Environment

Experiments were carried out in a greenhouse environment to assess the effect of APM-1 against damping-off disease of radish and cabbage seedlings. Damping-off disease is caused by *Rhizoctonia solani*. APM-1 inoculated particles were prepared as described in Example 2, using AXIS™-XT particles. The inoculated particles were mixed with Fafard® growing medium (Fafard, Agawam, Mass.) at a ratio of 1:9 (v/v) in the top layer of the medium where the radish and cabbage seeds were planted. APM-1 inoculated particles effectively suppressed damping-off disease of radish and cabbage seedlings when observed at the two-leaf stage.

EXAMPLE 5

Effect of APM-1 on Fungal Growth Under Field Conditions

APM-1 inoculated particles, prepared as described in Example 2 with AXIS™-XT particles, were tested at a turfgrass research facility in Massachusetts. Trials were initiated the second week of June and were completed on the last week in September. The following variables were tested in the experiment:
A. Application Rate: APM-1 particles at 1.25, 2.5, 5.0 and 10.0 lbs/1000 sq. ft.
B. Application Frequency: Once weekly and once every two weeks.
C. Application method: Surface broadcast (topical) application and high pressure injection. (Modified hydroject application)
E. Fertilizer Amendment: Inoculated particles and inoculated particles plus pelletized organic fertilizer.
F. Turf profile: U.S. Golf Association (USGA) sand, 70/30 sand/native soil, and native soil.

The turfgrass in all treatments was creeping bentgrass (*Agrostris palustris*). The experiment was conducted using a randomized, complete block design. Controls consisted of untreated plots. There were 3 replications of each treatment.

Each treatment was evaluated for overall turfgrass quality (blade color, plant density, U.S. Department of Agriculture National Turfgrass Evaluation Program standards.) Fungal disease in each treatment was also evaluated by visual examination and expressed as a percentage of the area affected. In addition, the persistence of APM-1 in the soil of each treatment was determined by carrying out population counts of APM-1 in each soil plot at the end of the experiment.

The weather patterns for the experiment promoted the initiation and proliferation of a number of turf diseases, due to increased average temperatures/humidity and to prolonged drought periods during which irrigation was utilized. These weather conditions allowed assessment of APM-1 as a potential inhibitor of turf disease, particularly dollar spot. Dollar spot disease is caused by *Sclerotinia homeocarpa.* The extent of dollar spot disease was much more pronounced on the USGA sand green plots compared to the sand/native soil plots and the pure native soil green plots, due to the lower fertility levels associated with sand greens. The occurrence of other fungal diseases was sporadic and permitted only qualitative assessment of the efficacy of APM-1. For instance, brown patch (*Rhizoctonia*) outbreaks did occur but for comparatively short time periods and were not equally distributed over the experimental plots.

The results of the field trials indicated that APM-1 inoculated particles were effective in maintaining overall turf quality and in suppressing dollar spot disease. Qualitative observations during the experiment indicated that APM-1 inoculated particles were also effective in suppressing brown patch disease. The results also indicated that an application rate of 5.0 and 10.0 lb APM-1 inoculated particles/1000 $ft^2$ were the most effective. The 10.0 lb rate appeared to be slightly better than the 5.0 lb rate. Both weekly and biweekly application frequencies appeared to be effective in maintaining overall turfgrass quality and suppressing fungal disease, although weekly treatment appeared to be slightly more effective. High pressure injection of APM-1 inoculated particles appeared to have no beneficial effect, whereas topical (foliar) application with a fertilizer spreader did appear to be effective. APM-1 inoculated particles combined with an organic fertilizer provided better overall turf quality and disease suppression compared to the use of APM-1 inoculated particles without an organic fertilizer.

Greens having a higher percentage of native soil had less disease activity and higher overall turfgrass quality ratings. Nevertheless, application of APM-1 inoculated particles was effective in suppressing fungal disease on all the tested greens types. Disease suppression was particularly noticeable on the USGA sand greens, where disease occurrence was comparatively very high and fertility levels were lower.

Application of APM-1 inoculated particles was found to be as effective or more effective than chlorothalonil (Daconil™) and propiconazole (Banner™) treatments every 14 days. The use of APM-1 inoculated particles provided more consistent long-term dollar spot control as well as increased turf quality. This was especially apparent with foliar APM-1 applications.

Plots treated with APM-1 particles and organic fertilizer sources showed better overall turf quality and less disease compared to plots treated with APM-1 particles alone. Population counts of APM-1 were also found to be higher in such plots, compared to plots treated with APM-1 particles alone.

EXAMPLE 6

Efficacy of a Toxin-Degrading Microorganism Composition

Experiments are carried out to assess the ability of a microorganism to degrade toxaphene. AXIS™-XT particles are prepared and inoculated with a putative toxin-degrading microorganism, using the techniques described in Example 2. Toxaphene is added to potting soil at about 1250 μg toxaphene per 50 gm of potting soil. The inoculated particles are mixed with the contaminated potting soil at a ratio of 1:9 (w/w). For comparison, stationary phase cells of the microorganism are mixed with contaminated potting soil at a ratio of 1:9 (w/w). After incubating for one week at room temperature under aerobic conditions, the amount of toxaphene present is measured using EPA method 8270 as described in U.S. Pat. No. 5,908,774. The experiment is repeated, using PROFILE™ particles.

EXAMPLE 7

Effect of APM-1 on Growth of *Candida* and *Aspergillus*

Experiments are carried out to assess the effect of APM-1 against *Candida*. A stationary phase culture of APM-1 is prepared as described in Example 2. About ten μl of the stationary phase bacterial suspension are inoculated onto each of six sterilized filter discs placed around a petri plate about 0.8 cm from the edge. A stationary phase culture of *Candida* is placed in the center of each plate. A plate containing sterilized media without APM-1 is used as a control. Plates are incubated at room temperature for seven days. The effectiveness of APM-1 in inhibiting fungal growth is measured based on the presence or absence of a clearance zone around each disc. The experiment is repeated, using *Aspergillus* in place of *Candida*.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising about $10^3$ cfu to about $10^{11}$ cfu of a bacterial strain per gram dry inert carrier, wherein said bacterial strain is designated AMP-1, deposited as ATCC Accession No. PTA-4838.

2. The composition of claim 1, wherein said carrier comprises porous, ceramic particles.

3. The composition of claim 2, wherein from about 20% to about 100% of said particles have a pore size of from about 0.5 μm to about 5 μm.

4. The composition of claim 1, further comprising about 5% to about 40% growth medium per gram of carrier on a wt/wt dry basis.

5. The composition of claim 1, wherein said bacterial strain exhibits degradative activity towards a toxin selected from the group consisting of polyaromatic hydrocarbons, aliphatic hydrocarbons, alicyclic hydrocarbons, polychlorinated biphenyls, aromatic hydrocarbons, alcohols, ethers, ketones, herbicides, insecticides, DDT, dieldrin, toxaphene, 1,1,1-trichloroethane, 1,1 dichloroethane, trans-1,2 dichloroethene, trichloroethylene, methylene chloride, toxaphene, dieldrin, lindane, aldrin, chlordane, endrin, endrin aldehyde, heptachlor, heptachlor epoxide, alpha-BHC, beta-BHC, gamma-BHC, delta-BHC, 4,4'-DDD, 4,4'-DDE, 4,4'-DDT, endosulfan I, endosulfan II, and endosulfan sulfate.

6. The composition of claim 1, wherein said bacterial strain exhibits fungicidal or fungistatic activity when applied to a soil environment.

7. The composition of claim 1, wherein said bacterial strain exhibits fungicidal or fungistatic activity towards a fungal plant pathogen.

8. A biologically pure culture of a bacterial strain designated APM-1, deposited as ATCC Accession No. PTA-4838.

* * * * *